(12) United States Patent
Lovejoy et al.

(10) Patent No.: US 6,519,484 B1
(45) Date of Patent: Feb. 11, 2003

(54) PULSE OXIMETRY SENSOR

(75) Inventors: David Anthony Lovejoy, Thiensville, WI (US); George Alexander Byers, Milwaukee, WI (US)

(73) Assignee: GE Medical Systems Information Technologies, Inc., Waukesha, WI (US)

( * ) Notice: Subject to any disclaimer, the term of this patent is extended or adjusted under 35 U.S.C. 154(b) by 25 days.

(21) Appl. No.: 09/704,169

(22) Filed: Nov. 1, 2000

(51) Int. Cl.[7] .................................................. A61B 5/00
(52) U.S. Cl. ........................................ 600/323; 600/344
(58) Field of Search .............................. 600/309–310, 600/322–324, 344

(56) References Cited

U.S. PATENT DOCUMENTS

| | | | |
|---|---|---|---|
| 5,094,240 A | * 3/1992 | Muz | 600/324 |
| 5,096,669 A | * 3/1992 | Lauks et al. | 204/403.2 |
| 5,413,099 A | * 5/1995 | Schmidt et al. | 600/310 |
| 5,429,129 A | * 7/1995 | Lovejoy et al. | 600/310 |
| 5,911,689 A | * 6/1999 | Smith et al. | 600/310 |
| 6,061,584 A | 5/2000 | Lovejoy et al. | |

* cited by examiner

Primary Examiner—Eric F. Winakur
Assistant Examiner—Matthew Kremer
(74) Attorney, Agent, or Firm—Michael Best & Friedrich LLP

(57) ABSTRACT

A physiologic condition sensor comprises a sensor body including an optical assembly housed in a sensor housing. The optical assembly is configured to include a head portion, a tail portion, and an intermediate portion connecting the head portion and tail portion. The head and tail portions are wider than the intermediate portion to prevent longitudinal deformation of the sensor housing around the optical assembly.

32 Claims, 11 Drawing Sheets

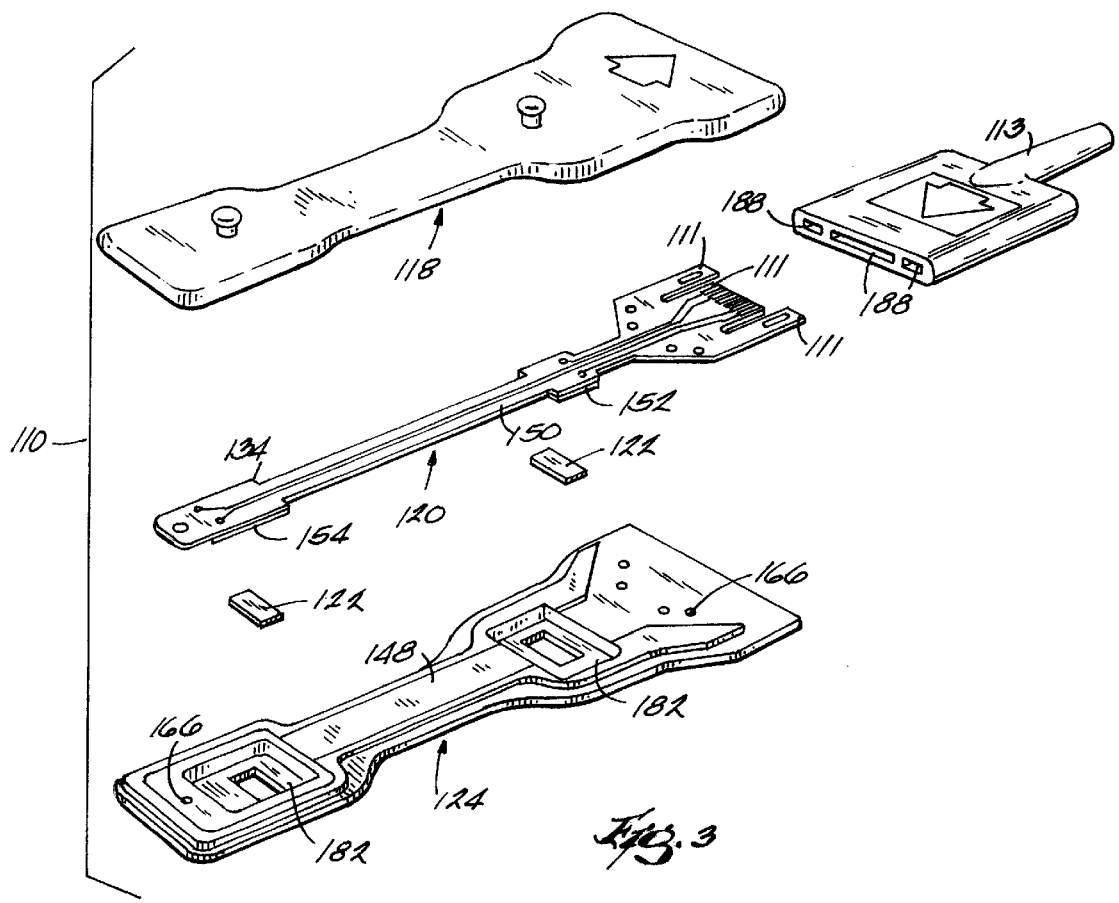

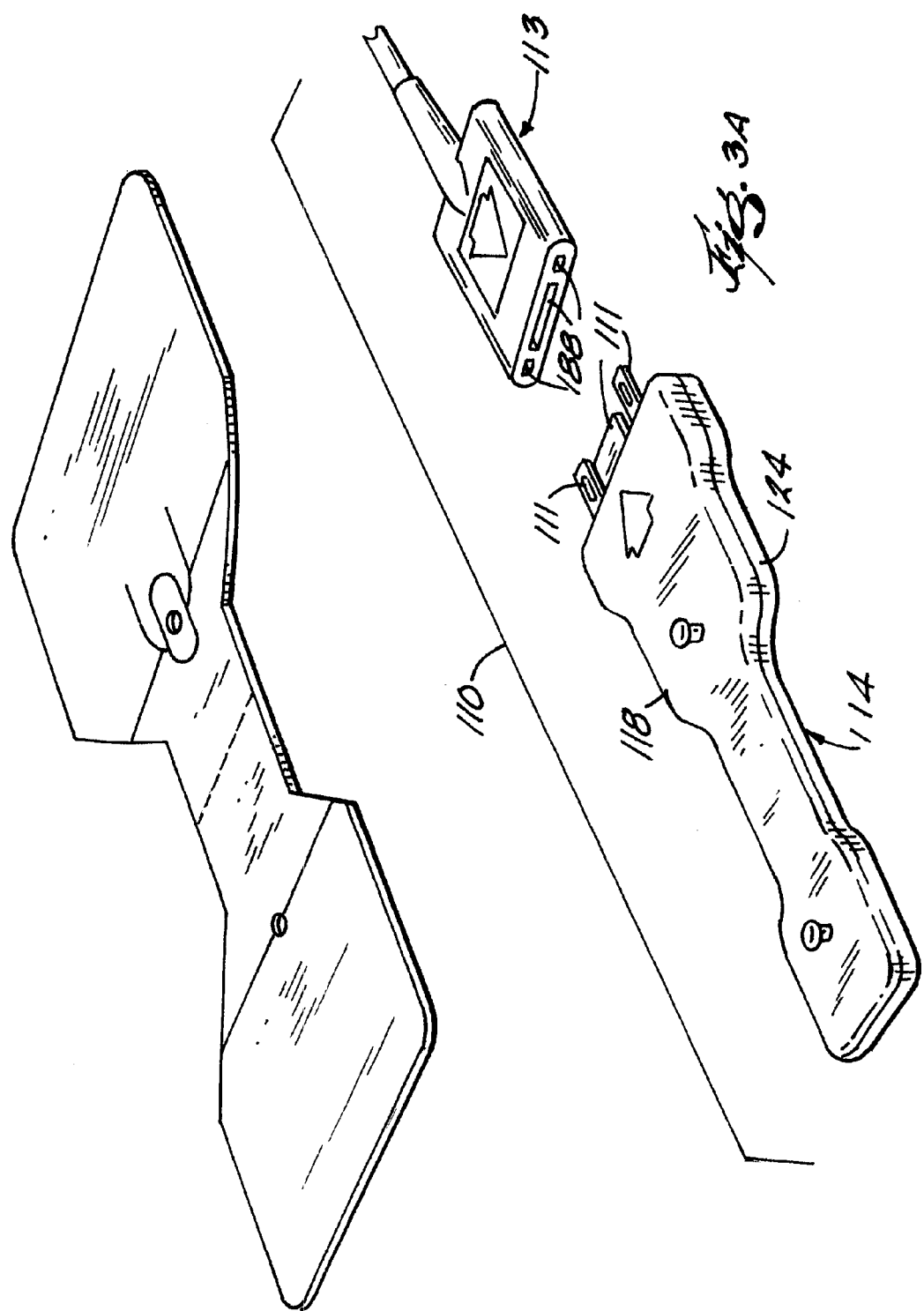

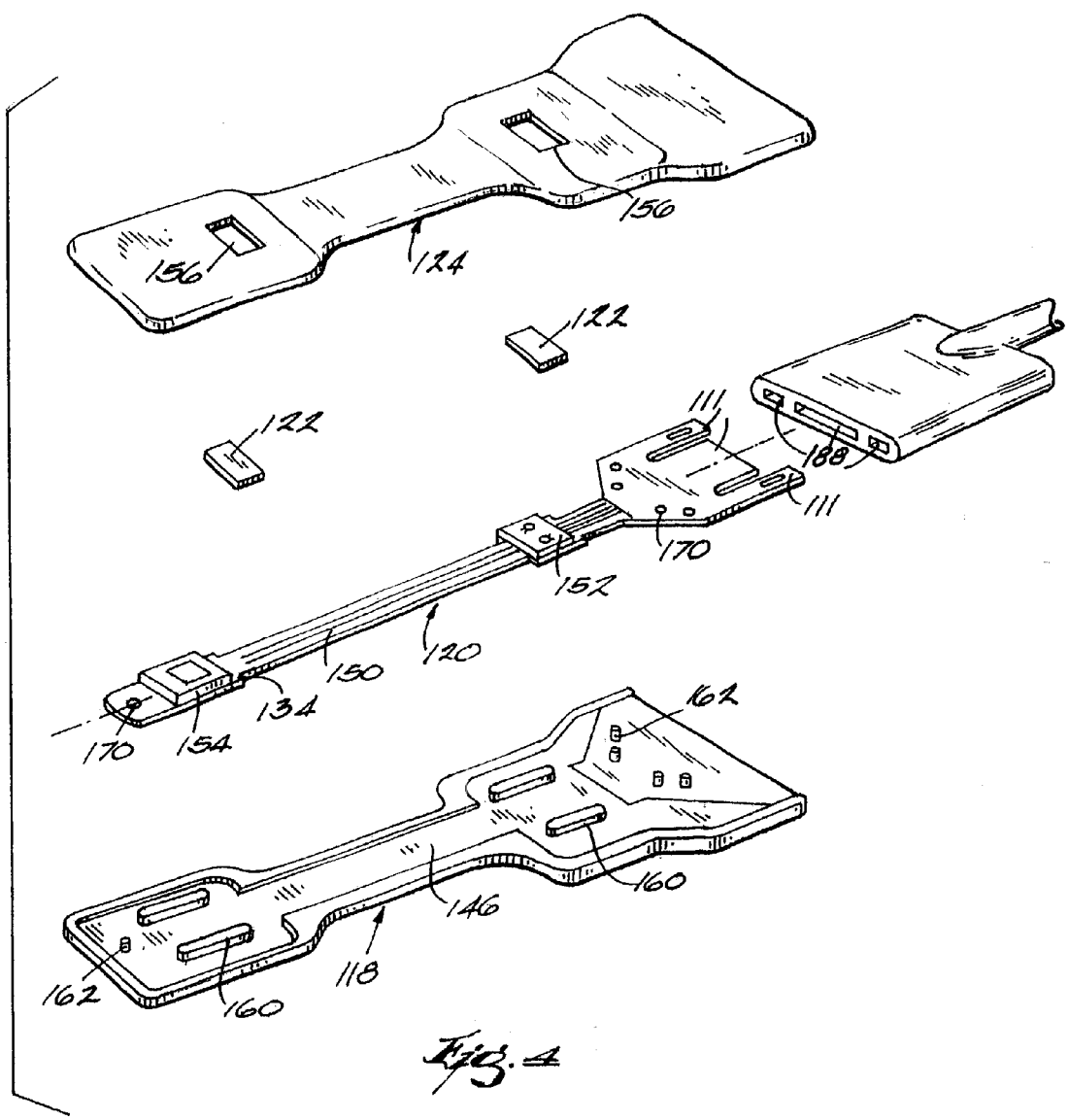

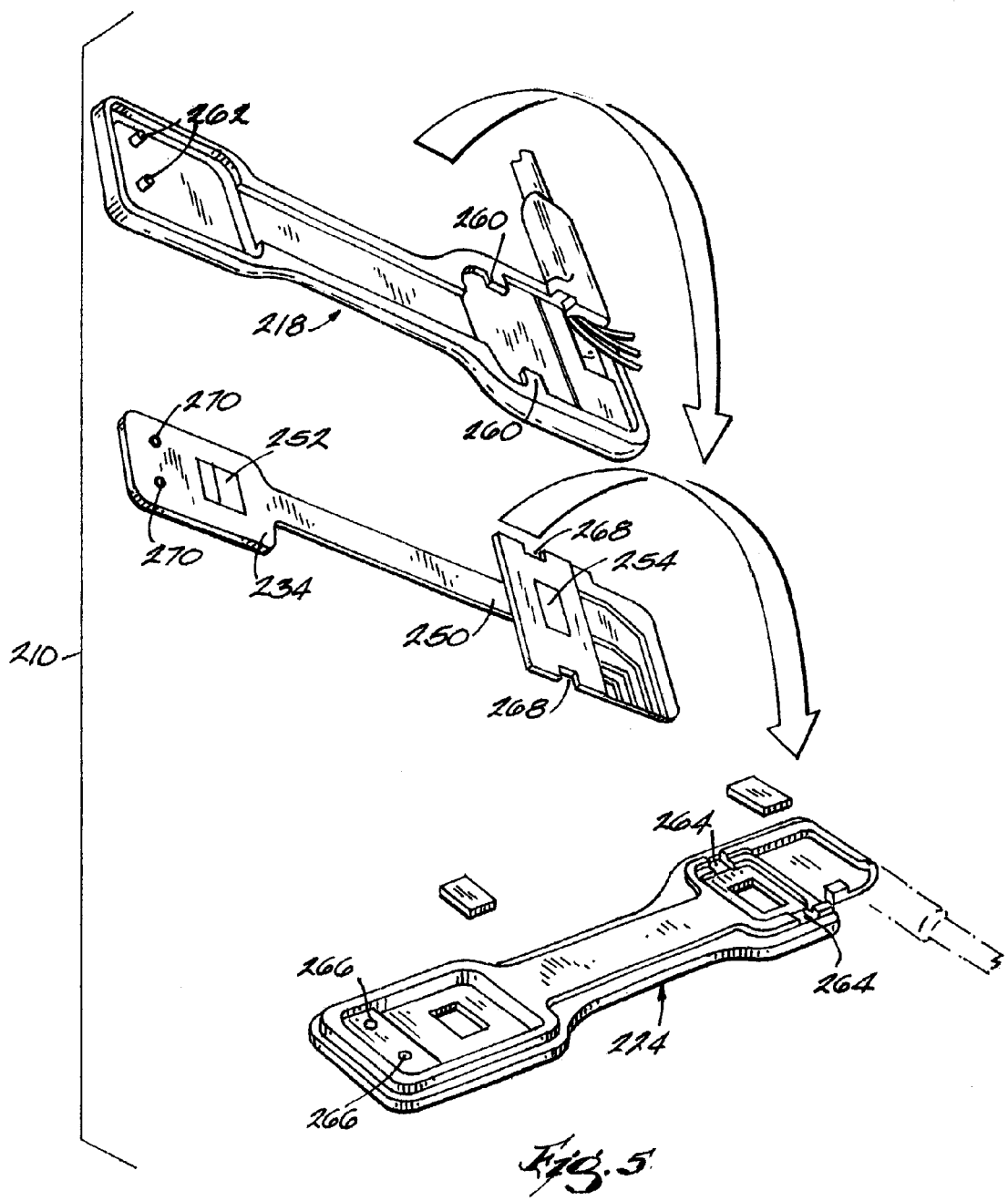

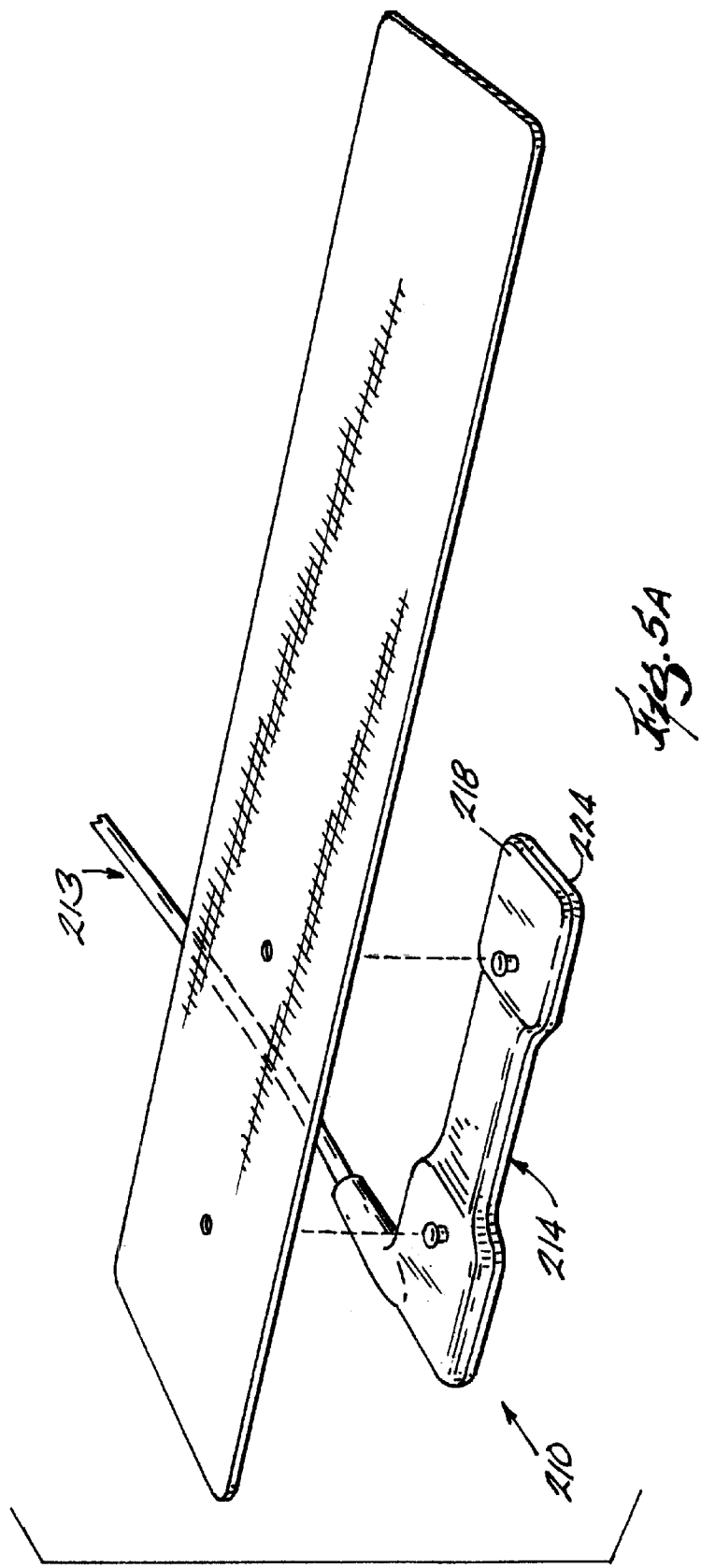

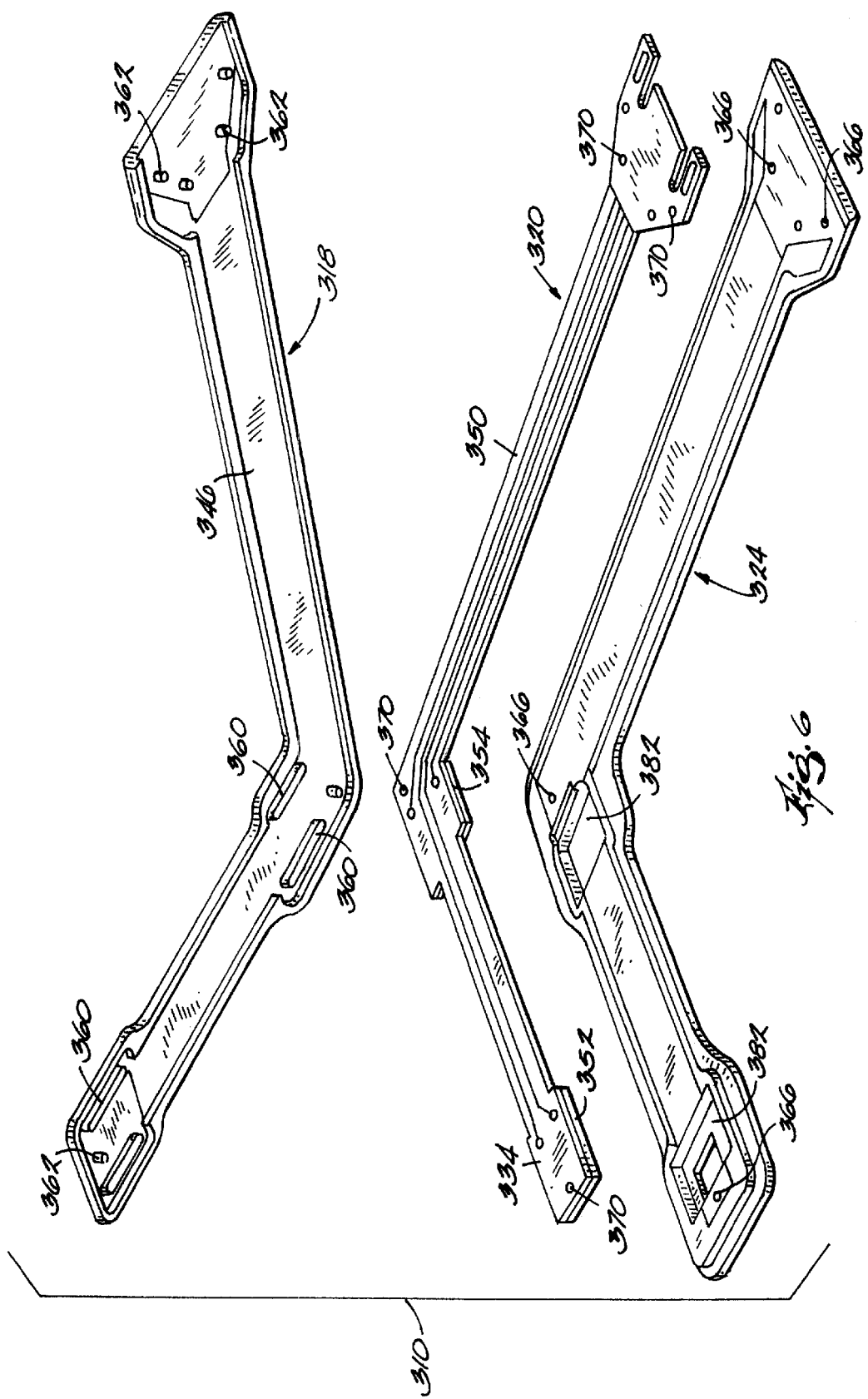

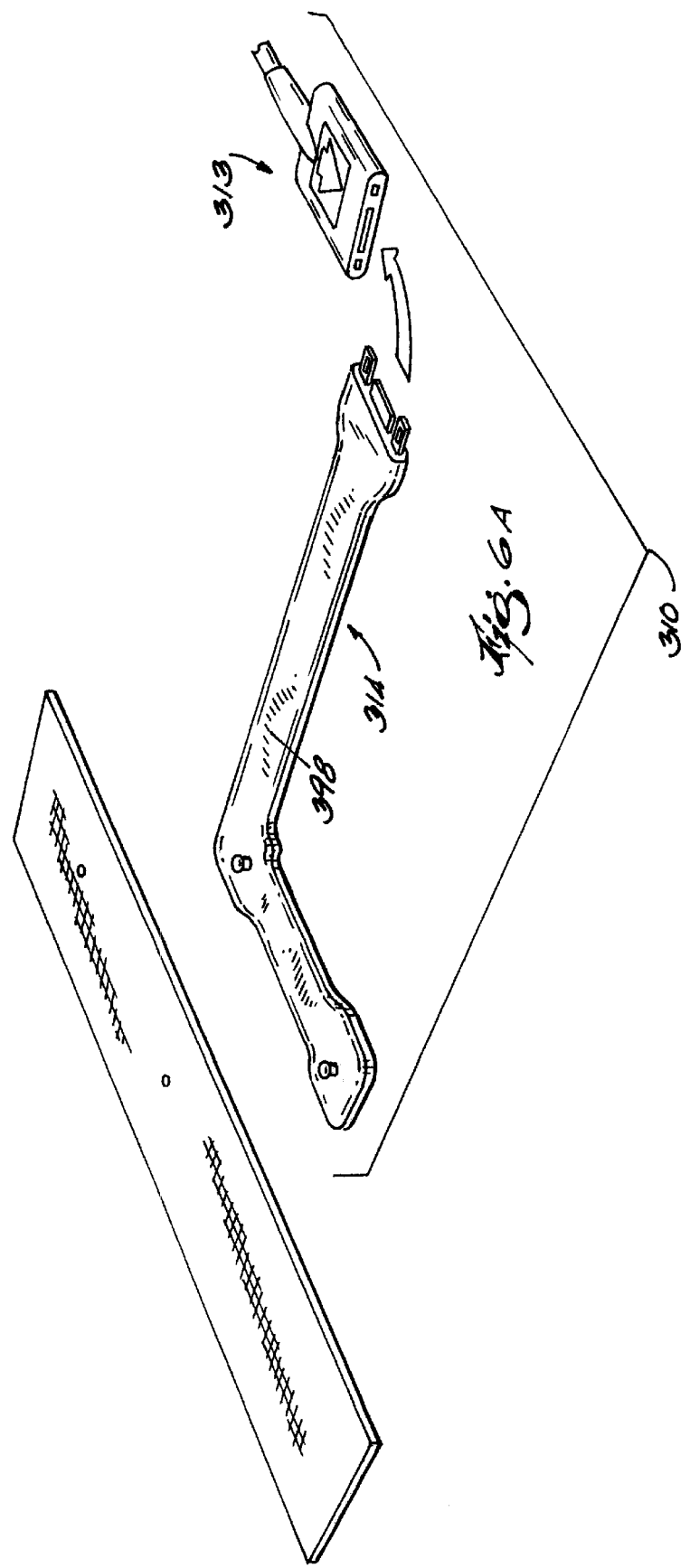

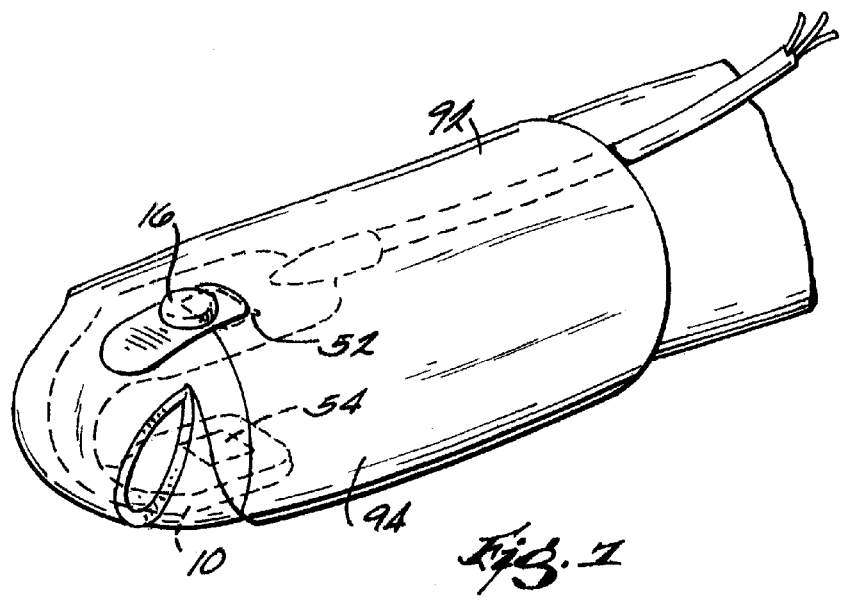
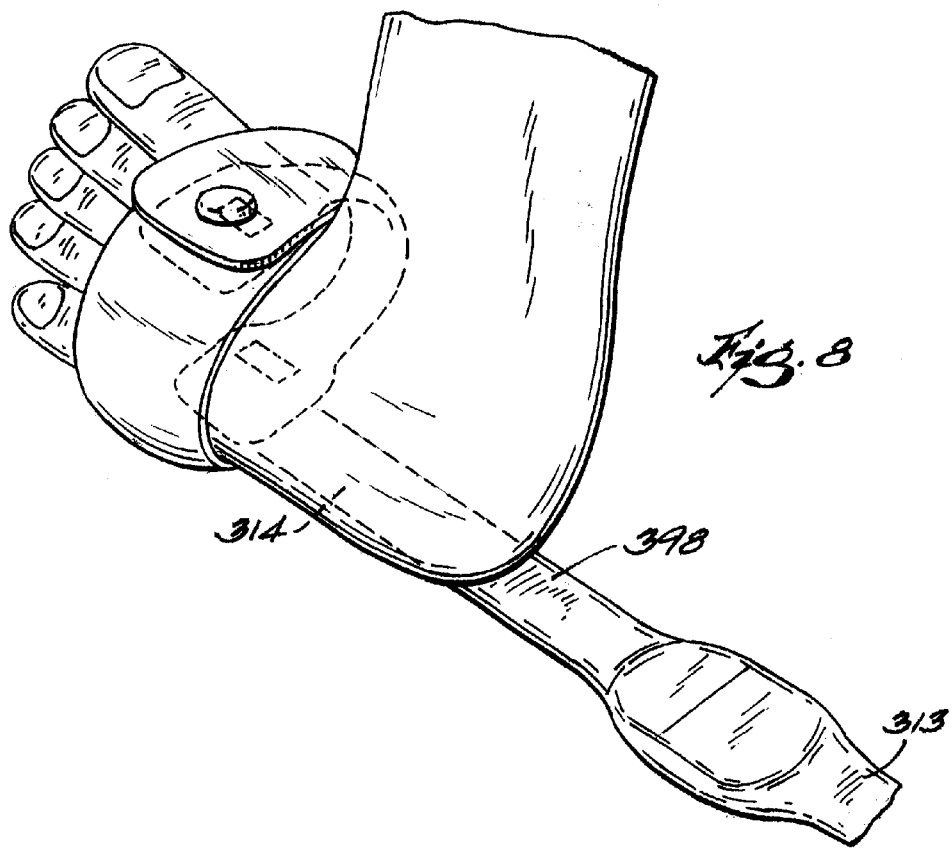

PULSE OXIMETRY SENSOR

This invention relates to noninvasive physiologic condition sensors, and more particularly, to noninvasive pulse oximetry sensors.

Noninvasive pulse oximetry typically takes advantage of the difference in the red and infrared light absorption coefficient of unoxygenated hemoglobin and oxygenated hemoglobin. This type of oximetry is normally conducted using sensors placed on the tissue of a patient. The sensors normally include a source for emitting light at one or more wavelengths placed on one side of a patient's tissue and a photodetector for detecting the amount of light which passes through the patient's tissue on the opposite side of the patient's tissue. The amount of light absorbed at each wavelength is used to calculate oxygen saturation in the patient's blood in accordance with Lambert-Beer's law. Such sensors are normally placed on the toe, foot, fingertip, ear lobe, nasal septum or forehead of the patient and preferably include means for retaining the sensor in position for the extended periods during which such measurements are made.

One type of prior art pulse oximetry sensor is disclosed in U.S. Pat. No. 6,061,584, the disclosure of which is incorporated by reference herein.

SUMMARY OF THE INVENTION

According to the present invention, a physiologic condition sensor comprises a sensor body including an optical assembly housed in an internal cavity of a sensor housing. The optical assembly includes a light emitting diode (LED) mounted at one end of a substrate and a photodetector mounted at the other. The optical assembly is configured to include a head portion, a tail portion, and an intermediate portion connecting the head portion and tail portion. The head and tail portions are wider than the intermediate portion to conform to the patient's anatomy and to prevent longitudinal deformation of the sensor housing around the optical assembly.

In a preferred embodiment, the sensor housing comprises a base and a cover. The base is configured to include a channel into which the optical assembly snuggly nests. This facilitates a tight fit of the optical assembly in the sensor housing and provides easy and exacting assembly of the sensor body. The cover is configured to include a plateau that fits within the channel in the base and cooperates with the channel to further provide a secure enclosure for the optical assembly.

In a preferred embodiment, lugs and posts formed in the channel, which cooperate with rooms and holes formed in the cover, engage the optical assembly to prevent longitudinal deformation of the cover and base of the sensor housing around the optical assembly. The seam at which the cover and base meet is configured to lie on a sidewall of the sensor body to give a uniform and seamless look to the sensor.

Additional features and advantages of the invention will become apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which:

FIG. 3 is an exploded, perspective view of a detachable adult finger sensor including a sensor base, an optical assembly, two lenses, and a sensor cover;

FIG. 3A is a perspective view of the detachable adult finger sensor of FIG. 3 assembled and an adhesive attachment pad;

FIG. 4 is an exploded, perspective view of the detachable adult finger sensor of FIG. 3, viewed from the side of the sensor opposite that viewed in FIG. 3, showing the sensor cover, the two lenses, the optical assembly, and the sensor base;

FIG. 5 is an exploded view of an integrated cable right-angle sensor for use on an infant, showing an optical assembly and the interior surfaces of a base and a cover;

FIG. 5A is a perspective view of the integrated cable right-angle infant sensor of FIG. 5 assembled and an adhesive attachment pad;

FIG. 6 is an exploded view of a detachable right-angle infant sensor, showing an optical assembly and the interior surfaces of a base and a cover;

FIG. 6A is a perspective view of the detachable right-angle infant sensor of FIG. 6 assembled and an adhesive attachment pad;

FIG. 7 is an integrated cable adult finger sensor shown in use on an adult finger; and FIG. 8 is a detachable right-angle infant sensor shown in use on an infant foot.

THE DETAILED DESCRIPTION OF PREFERRED EMBODIMENTS

Figure 1:
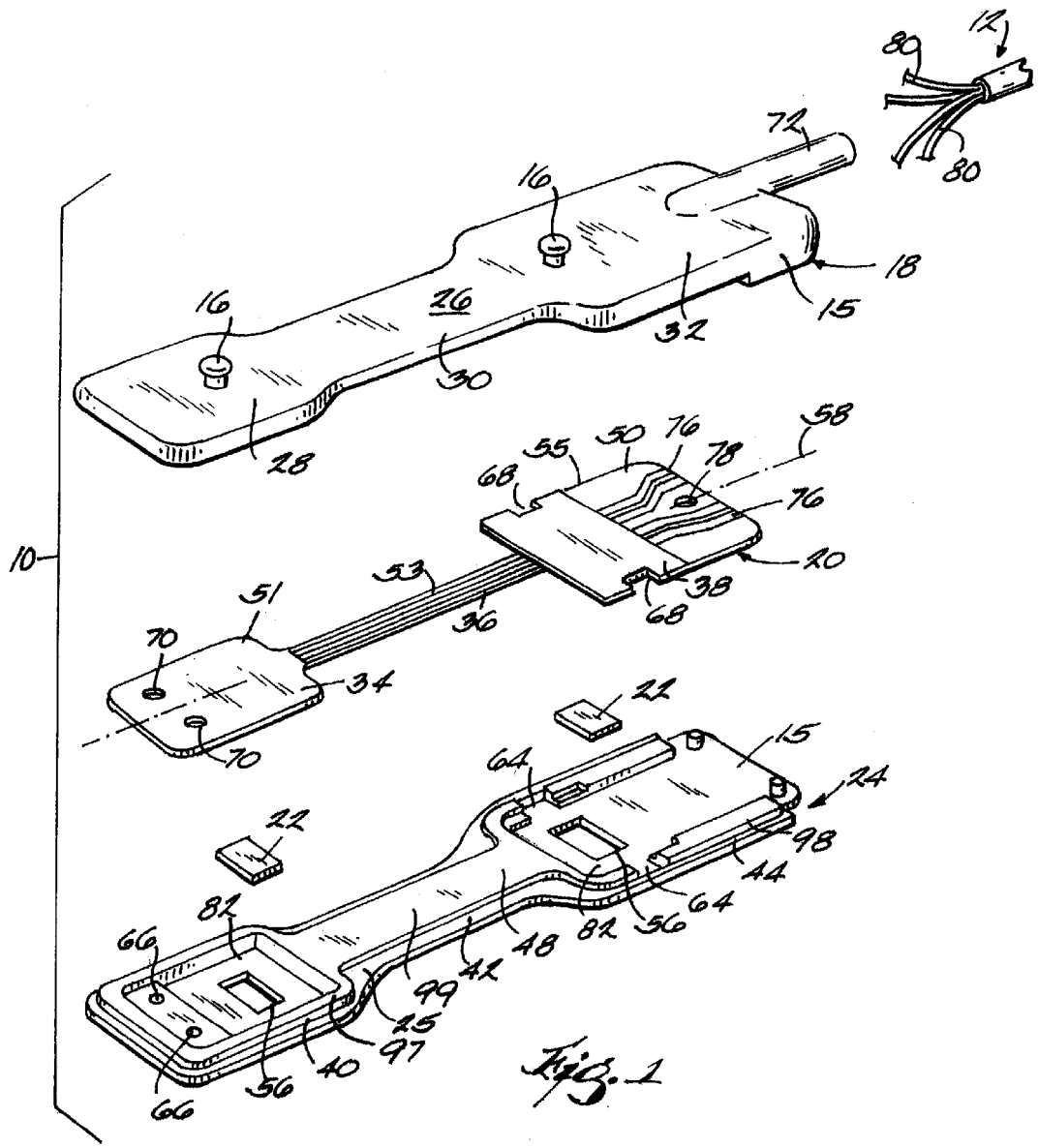
FIG. 1 is an exploded, perspective view of an integrated cable adult finger sensor including a sensor base, an optical assembly, two lenses, and a sensor cover.
Figure 1A:
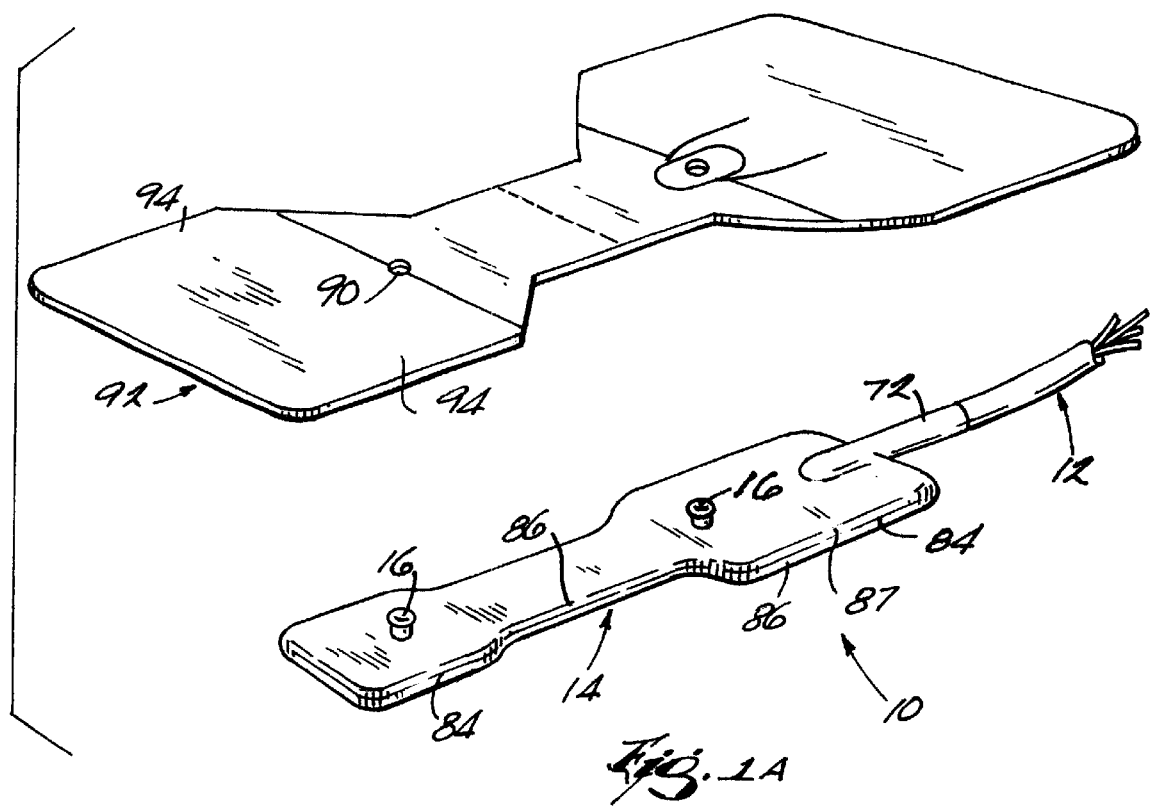
FIG. 1A is a perspective view of the integrated cable adult finger sensor of FIG. 1 assembled and an adhesive attachment pad.
Figure 2:
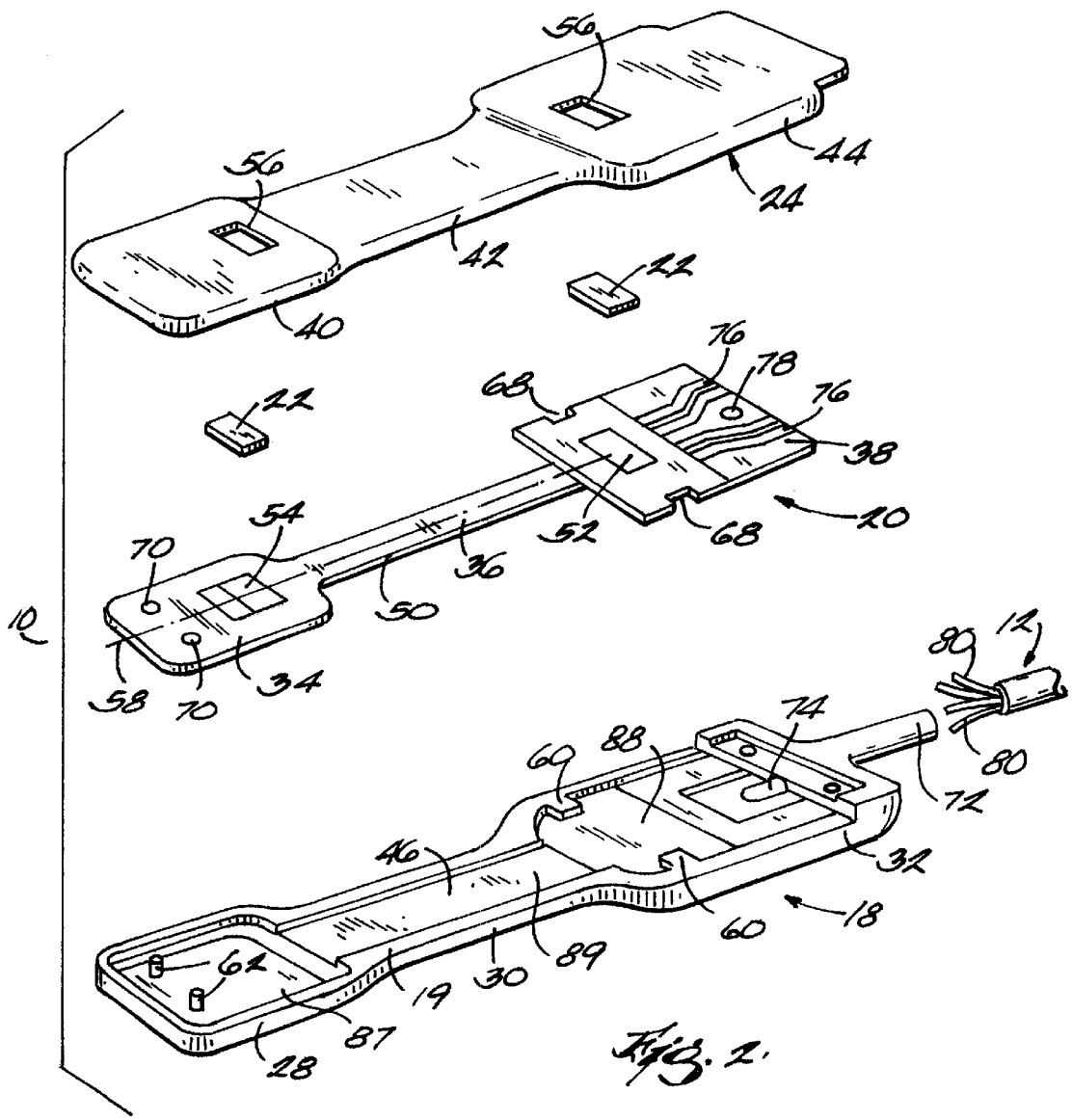
FIG. 2 is an exploded, perspective view of the integrated cable adult finger sensor of FIG. 1, viewed from the side of the sensor opposite that viewed in FIG. 1, showing the sensor cover, the two lenses, the optical assembly, and the sensor base.

Various embodiments of patient condition sensors in accordance with the present invention are shown in FIGS. 1 through 8. FIGS. 1 and 2 illustrate exploded views, taken in opposite directions, of an integrated cable adult finger sensor 10. The integrated cable adult finger sensor 10 includes a sensor body 14 and a sensor cable 12 (FIG. 1A). The sensor body 14 comprises a sensor base 18, an optical assembly 20, two lenses 22, and a sensor cover 24. When assembled, the integrated cable adult finger sensor 10 includes the sensor cable 12 affixed to the sensor body 14 as a single integrated unit (FIG. 1A). In use, the integrated cable adult finger sensor 10 is affixed to a patient's finger, as shown in FIG. 7. Mushroom-shaped mounting members 16 on an exterior surface 26 of the sensor base 18 are inserted through apertures 90 in an adhesive pad 92 to connect the integrated cable adult finger sensor 10 to the adhesive pad 92 (FIG. 1A). As shown if FIG. 7, the integrated cable adult finger sensor 10 is then folded over the fingertip of a patient and wings 94 of the adhesive pad 92 are wrapped around the patient's finger to secure the integrated cable adult finger sensor 10 in place (FIG. 7).

FIGS. 1 and 2 illustrate the integrated cable adult finger sensor 10. However, FIGS. 1 and 2 are also illustrative of an integrated cable pediatric finger sensor (not shown) for use on children, which differs from the integrated cable adult finger sensor 10 only in size.

FIGS. 3, 3A, and 4 illustrate another embodiment of the present invention in the form of a detachable adult finger sensor 110. The detachable adult finger sensor 110 is similar to the integrated cable adult finger sensor 10 (FIGS. 1 and 2), except that, unlike the integrated cable adult finger sensor 10, the sensor cable 12 is not included as an integrated part of the detachable adult finger sensor 110. Instead, the detachable adult finger sensor 110 includes connection prongs 111 which allow it to be connected to an extension cable 113 which serves the same purpose as the sensor cable 12 integrated into the integrated cable adult finger sensor 10. The detachable adult finger sensor 110 allows for disposal of its sensor body 114 without requiring disposal of the reusable extension cable 113 (FIG. 3A).

Again, as with the integrated cable adult finger sensor 10, the detachable adult finger sensor 110, shown in FIGS. 3 and 4, is also illustrative of a detachable pediatric finger sensor (not shown) for use on children, which differs from the detachable adult finger sensor 110 only in size.

FIGS. 5 and 6 illustrate still additional embodiments of the present invention in the form of an integrated cable right-angle sensor 210 and a detachable right-angle sensor 310, respectively. The difference between the integrated cable right-angle sensor 210, shown in FIG. 5, and the detachable right-angle sensor 310, shown in FIG. 6, is that the sensor body 314 of the detachable right-angle sensor 310, shown in FIG. 6A, may be disposed of without simultaneously having to discard its extension cable 313. By contrast, disposal of the sensor body 214 of the integrated cable right-angle sensor 210 requires disposal of the affixed sensor cable 213. Right-angle sensors, as shown in FIGS. 5 and 6, are used on infants and newborns. Because of the small size of an infant's fingers, finger sensors, such as those shown in FIGS. 1 through 4, are unwieldy and impractical. Therefore, patient condition sensors are instead placed on a larger body part of an infant. As shown in FIG. 8, the detachable right-angle sensor 310 is placed on an infant's foot.

Both the integrated cable right-angle sensor 210, shown in FIGS. 5 and 5A, and the detachable right-angle sensor 310, shown if FIGS. 6, 6A and 8 are for infants. However, right-angle sensors for neonatal use (not shown) differ from the right-angle sensors for infants 210 and 310, shown in FIGS. 5, 5A, 6, 6A, and 8 only in size.

Referring back to FIGS. 1, 1A, and 2, in accordance with a presently preferred embodiment of the invention, the sensor body 14 includes the optical assembly 20, two lenses 22, and a sensor housing 15 comprising the sensor base 18 and the sensor cover 24. The base 18, optical assembly 20, and cover 24 are similarly shaped. The base 18 includes a head portion 28, an intermediate portion or link 30, and a tail portion 32. Similarly, the optical assembly 20 includes a head portion 34, an intermediate portion or link 36, and a tail portion 38. And, lastly, the cover 24 includes a head portion 40, an intermediate portion or link 42, and a tail portion 44.

The sensor base 18 includes a channel 46, as shown in FIG. 2, and the cover 24 includes a plateau 48, as shown in FIG. 1. The channel 46 and plateau 48 are each shaped substantially like the sensor base 18 and cover 24 to include head 87, 97, tail 88, 98, and intermediate 89, 99 portions which mate with each other to insure proper alignment and a tight fit of the base 18 and cover 24 when assembled. Additionally, as shown in FIG. 2, the optical assembly 20 is shaped to nest within the channel 46 of the base 18 so that it too is properly aligned with the cover 24 and base 18. In this way, the optical assembly 20 is housed within an internal cavity of the sensor housing which is created when the plateau 48 of the cover 24 mates with the channel 46 of the sensor base 18. This internal cavity includes a head chamber, a tail chamber, and an intermediate chamber similarly shaped to, and resulting from the mating of, the head 87, 97, tail 88, 98, and intermediate 89, 99 portions of the channel 46 and the plateau 48. However, it will be readily apparent to one of ordinary skill in the art that the internal cavity (with its head, tail, and intermediate chambers) could be formed in a one-piece housing, rather than a housing having a separate base 18 and cover 24.

The optical assembly 20 includes a Kapton(V substrate 50 including a head portion 51, a tail portion 55, and an intermediate portion or link 53, on which an LED assembly 52, including a red emitting LED and an infrared emitting LED, and a photodetector 54 are mounted (FIG. 2). With the integrated cable adult finger sensor 10 folded over the tip of a patient's finger, as shown in FIG. 7, the LED assembly 52 and photodetector 54 are aligned on opposite sides of the patient's finger. In this arrangement, light from the LED assembly 52 is shown through the patient's finger and received by the photodetector 54. As can be seen in FIG. 2, it is therefore important that the photodetector 54 and LED assembly 52 are properly aligned with two windows 56 formed in the cover 24 of the sensor body 14. This insures that the sensor body 14 in no way obstructs light from the LED assembly 52 from reaching the photodetector 54.

The Kapton® substrate 50 of the optical assembly 20 helps insure proper alignment of the various constituent parts. The head portion 34 and tail portion 38 of the optical assembly 20 fit within the respective head portions 28, 40 and tail portions 32, 44 of the sensor base 18 and sensor cover 24, respectively, and are wider than the intermediate portions 36, 42, 30 of the optical assembly 20, cover 24, and base 18. Moreover, the substrate 50 of the optical assembly 20 has virtually no elasticity along its longitudinal axis 58. Therefore, the substrate 50 serves as a "back bone" for the sensor body 14 around which the very flexible base 18 and cover 24 cannot longitudinally deform. The wider head portion 34 and tail portion 38 of the optical assembly 20, with its longitudinally inelastic substrate 50, prevent the sensor cover 24 and sensor base 18 from "sliding" longitudinally up and down the more narrow intermediate portion 36 of the optical assembly 20. In this way, proper alignment of the various sensor parts is achieved and the LED assembly 52 and photodetector 54 remain positioned in line with the windows 56 in the sensor cover 24 when the sensor body 14 is assembled.

Additionally, the integrated cable adult finger sensor 10 includes lugs 60 and posts 62 in the sensor base 18 (FIG. 2) which cooperate with rooms 64 and cover holes 66 in the sensor cover 24 (FIG. 1) to insure proper alignment of the base 18 relative to the cover 24. As is readily apparent with reference to FIGS. 1 and 2, the lugs 60 and posts 62 also insure proper alignment of the optical assembly 20 relative to the sensor base 18 and sensor cover 24. The lugs 60 in the sensor base 18 fit within substrate notches 68 in the tail portion 38 of the optical assembly 20 preventing longitudinal movement of the optical assembly 20 within the channel 46 of the sensor base 18. As mentioned, in addition to the notches 68, the lugs 60 further mate with the rooms 64 in the sensor cover 24 when the sensor body 14 is assembled. Further, posts 62 in the sensor base 18 extend through substrate holes 70 in the head portion 34 of the optical assembly 20 and mate with the cover holes 66 in the sensor cover 24, further preventing longitudinal misalignment of the sensor base 18 or sensor cover 24 with respect to the optical assembly 20.

To assemble the integrated cable adult finger sensor 10 shown in FIG. 1A, the sensor cable 12, shown in FIG. 1, is first threaded through an entryway 72 formed as an integral part of the sensor base 18 and out an interior aperture 74 in the base 18 (FIG. 2). After being threaded through the entryway 72, wires 80 within the sensor cable 12 are attached to electronic leads 76 on the substrate 50. Additionally, a Kevlar® strength member (not shown) within the sensor cable 12 is tied to the substrate 50 through a strengthening hole 78 in the substrate 50 so that forces acting between the optical assembly 20 and sensor cable 12 are not carried by the connection between wires 80 and electronic leads 76, but are instead carried by the Kevlar® strength member. Once the sensor cable 12 is thus connected to the optical assembly 20, the cable 12 is pulled back through the entryway 72 until the optical assembly 20 is properly positioned within the channel 46 of the sensor base 18.

Separately, the two discrete silicon lenses 22 are placed in wells 82 surrounding the windows 56 of the sensor cover 24 and are glued in place. The sensor cover 24, with lenses 22 thus glued in place, is then positioned over the sensor base 18, with included optical assembly 20. Next, the lugs 60 and posts 62 are aligned and fitted into their respective rooms 64 and cover holes 66, the plateau 48 is seated in the channel 46, and a sealing ledge 25 of the cover 24 is glued to a sealing lip 19 of the base 18. In this way, as shown in FIG. 1A, a seam 84 is formed substantially around the outside of the resulting sensor body 14 on sidewalls 86 and 87 of the sensor body 14, thereby providing a finished look. However, the seam 84 does not extend to the entryway 72. Thus, the entryway 72 remains as an integral part of the sensor base 18 and has no connection seam. This lessens the possibility of delamination at the entryway 72, which might otherwise exist if the entryway 72 were constructed of two parts with a seam between them.

Referring to FIGS. 3, 3A and 4, in accordance with the invention, the detachable adult finger sensor 110 contains various alignment and assembly features. As shown in FIG. 3, the sensor body 114 includes a sensor base 118 and optical assembly 120, two lenses 122 and a sensor cover 124. As with the integrated cable adult finger sensor 10, the sensor base 118 of the detachable adult finger sensor 110 includes a channel 146 (FIG. 4) which cooperates with a plateau 148 in the sensor cover 124 (FIG. 3). These features facilitate alignment and fit of the sensor cover 124 and sensor base 118 when assembled, as shown in FIG. 3A. The optical assembly 120 is shaped to fit snuggly within the channel 146 in sensor base 118. As with the integrated cable adult finger sensor 10, the detachable adult finger sensor 110 is formed to include posts 162 (FIG. 4) which fit through substrate holes 170 and engage cover holes 166 in the sensor cover 124 (FIG. 3). In this way, the optical assembly is securely held between the channel 146 and the plateau 148.

The optical assembly 120 comprises a substrate 150 on which an LED assembly 152 and photodetector 154 are mounted. Again, as with the integrated cable adult finger sensor 10 shown in FIGS. 1, 1A and 2, it is important that the LED assembly 152 and photodetector 154 are properly aligned with windows 156 in the sensor cover 124. The cooperation of the posts 162, substrate holes 170, and cover holes 166 helps ensure this alignment. Additionally, alignment lugs 160 aid in guiding and aligning the optical assembly 120 by flanking the substrate 150 and fitting into lens wells 182 in the sensor cover 124.

Referring to FIG. 3A, with the sensor body 114 assembled, the sensor base 118 and sensor cover 124 house the entire optical assembly 120 except for connection prongs 111 formed in the substrate 150 which extend beyond the base 118 and cover 124. The prongs 111 fit within slots 188 to connect the sensor body 114 to the extension cable 113 in any suitable matter such as is disclosed in U.S. Pat. No. 6,061,584 to Lovejoy et al., the disclosure of which is incorporated herein by reference.

As shown in FIGS. 5 and 5A, a sensor base 218 and sensor cover 224 of the integrated cable right-angle sensor 210 include similar features to the integrated cable adult finger sensor 10 shown in FIGS. 1, 1A and 2. Lugs 260 and posts 262 formed in sensor base 218 cooperate with rooms 264 and cover holes 266 in sensor cover 224 and substrate notches 268 and substrate holes 270 formed in a substrate 250 to facilitate proper alignment and fit of the various assembled parts of the integrated cable right-angle sensor 210. However, an LED assembly 252 and photodetector 254 are positioned differently than in the integrated cable adult finger sensor 10 shown in FIGS. 1, 1A and 2. The LED assembly 252 is positioned on a head portion 234 in the integrated cable right-angle sensor 210, whereas the photodetector 54 is positioned on the head portion 34 in the integrated cable adult finger sensor 10.

Lastly, as shown in FIGS. 6 and 6A, the detachable right-angle sensor 310 includes similar features to the detachable adult finger sensor 110 shown in FIGS. 3, 3A and 4, to ensure proper alignment and fit of the constituent parts of the detachable right-angle sensors 310 when assembled. Again, however, an LED assembly 352 and photodetector 354 are positioned differently than in the detachable adult finger sensor 110 shown in FIGS. 3, 3A and 4. The LED assembly 352 is positioned on a head portion 334 in the detachable right-angle sensor 310, whereas the photodetector 154 is positioned on a head portion 134 in the detachable adult finger sensor 110.

As shown in FIG. 6, a channel 346 of a sensor base 318 includes lugs 360 and posts 362 which cooperate with cover holes 366 and wells 382 to ensure a proper fit between the base 318 and cover 324. Additionally, the posts 362 fit through substrate holes 370 and the lugs 360 straddle a substrate 350 of the optical assembly 320 to ensure that the optical assembly 320 is also properly aligned between the sensor base 318 and sensor cover 324.

The only substantial difference between the detachable right-angle sensor 310 and the integrated cable right-angle sensor 210 is that the detachable right-angle 310 includes an extension arm 398 (FIG. 6A) while the integrated cable right-angle sensor 210 does not. The extension arm 398 provides an extension to move the point of connection between the sensor body 314 and extension cable 313 away from the sight on the patient where a reading is being taken (FIG. 8). The integrated cable right-angle sensor 210 does not require such an extension arm because the sensor cable 213 is integrated into the sensor body 214, eliminating the bulky connection between the sensor body 314 and extension cable 313 found in the detachable right-angle sensor 310.

Each of the detachable adult finger sensor 110, the integrated cable right-angle sensor 210, and the detachable right-angle sensor 310 includes various features which correspond to features found in the integrated cable adult finger sensor 10, discussed above. The corresponding features of these various embodiments operate in the same way as they do with respect to the integrated cable adult finger sensor 10. Each of the embodiments ensures proper fit and alignment and easy assembly of the constituent parts of the various sensor bodies.

Although the invention has been described in detail with reference to certain preferred embodiments, variations and modifications exists within the scope and spirit of the invention as described and defined in the following claims.

We claim:

1. A noninvasive pulse oximetry sensor comprising:
   a sensor housing having an internal cavity,
   an optical assembly housed within the cavity, the optical assembly including an LED, a photodetector, and a substrate, the substrate having substantially no elasticity in a direction along its longitudinal axis and being shaped to prevent substantial longitudinal movement of the sensor housing relative to the substrate;
   wherein the cavity includes a head chamber, a tail chamber, and an intermediate chamber connecting the head chamber to the tail chamber, the substrate has a head portion, a tail portion, and a link, all lying along the longitudinal axis, the link providing a connection between the head portion and the tail portion and being substantially narrower than the head portion and the tail portion, the LED being mounted to the tail portion and the photodetector being mounted to the head portion, and, with the optical assembly housed within the cavity, the head portion is positioned to lie within the head chamber, the tail portion is positioned to lie within the tail chamber, and the link is positioned to lie within the intermediate chamber;
   wherein the head portion and the tail portion of the substrate are substantially wider than the intermediate chamber of the cavity; and
   wherein the sensor housing is formed to further include a lug protruding into the tail chamber and the tail portion of the substrate is formed to further include a notch formed to receive the lug.

2. The sensor of claim 1, wherein the housing and optical assembly are bendable.

3. The sensor of claim 1, further including an entryway from the exterior of the sensor housing to the cavity, the entryway being in communication with the tail chamber.

4. The sensor of claim 1, further including an entryway from the exterior of the sensor housing to the cavity, the entryway being in communication with the head chamber.

5. The sensor of claim 1, wherein the head portion of the substrate includes an aperture and the housing is formed to further include a post protruding into the head chamber and through the aperture.

6. A noninvasive pulse oximetry sensor comprising:
   a sensor housing having an internal cavity,
   an optical assembly housed within the cavity, the optical assembly including an LED, a photodetector, and a substrate, the substrate having substantially no elasticity in a direction along its longitudinal axis and being shaped to prevent substantial longitudinal movement of the sensor housing relative to the substrate;
   wherein the cavity includes a head chamber, a tail chamber, and an intermediate chamber connecting the head chamber to the tail chamber, the substrate has a head portion, a tail portion, and a link, all lying along the longitudinal axis, the link providing a connection between the head portion and the tail portion and being substantially narrower than the head portion and the tail portion, the LED being mounted to the tail portion and the photodetector being mounted to the head portion, and, with the optical assembly housed within the cavity, the head portion is positioned to lie within the head chamber, the tail portion is positioned to lie within he tail chamber, and the link is positioned to lie within the intermediate chamber;
   wherein the head portion and the tail portion of the substrate are substantially wider than the intermediate chamber of the cavity; and
   wherein the sensor housing includes a lug protruding into the head chamber and the head portion of the substrate is formed to flyer include a notch formed to receive the lug.

7. The sensor of claim 6, wherein the tail portion of the substrate includes an aperture and the housing is formed to further include a post protruding into the tail chamber and through the aperture.

8. The sensor of claim 6, further including an entryway from the exterior of the sensor housing to the cavity, the entryway being in communication with the tail chamber.

9. The sensor of claim 6, further including an entryway from the exterior of the sensor housing to the cavity, the entryway being in communication with head chamber.

10. A noninvasive pulse oximetry sensor:
    a sensor housing including an internal cavity having a head chamber, a tail chamber, and an intermediate chamber connecting the head chamber to the tail chamber, and
    an optical assembly housed within the cavity, the optical assembly including an LED, a photodetector, and a substrate having substantially the same the cavity and defining a longitudinal axis, the substrate having substantially no elasticity in a direction along its longitudinal axis, the substrate having a head portion, a tail portion and a link, all lying along the longitudinal axis, the link providing a connection between head portion and the tail portion and being substantially narrower than the head portion and the tail portion, the LED being mounted to the tail portion and the photodetector being mounted to the head portion, wherein, with the optical assembly housed within the cavity, the head portion is positioned to lie within the head chamber, the tail portion is positioned to lie within the tail chamber, the link is positioned to lie within the intermediate chamber, and the head portion and the tail portion are substantially wider than the intermediate chamber; and
    wherein the head portion of the substrate includes an aperture and the housing is formed to further include a post protruding into the head chamber and through the aperture.

11. The sensor of claim 10, further including an entryway from the exterior of the sensor housing to the cavity, the entryway being in communication with the tail chamber.

12. The sensor of claim 10, further including an entryway from the exterior of the sensor housing to the cavity, the entryway being in communication with the head chamber.

13. The sensor of claim 10, wherein the sensor body includes a lug protruding into the tail chamber and the tail portion of the substrate is formed to further include a notch formed to receive the lug.

14. The sensor of claim 10, wherein the sensor body includes a lug protruding into the head chamber and the head portion of the substrate is formed to further include a notch formed to receive the lug.

15. A noninvasive pulse oximetry sensor:
    a sensor housing including an internal cavity having a head chamber, a tail chamber, and an intermediate chamber connecting the head chamber to the tail chamber, and
    an optical assembly housed within the cavity, the optical assembly including an LED, a photodetector, and a substrate having substantially the same shape as the cavity and defining a longitudinal axis, the substrate having substantially no elasticity in a direction along its longitudinal axis, the substrate having a head portion, a tail portion, and a link, all lying along the longitudinal axis, the link providing a connection between the head portion and the tail portion and being substantially narrower than the head portion and the tail portion, the LED being mounted to the tail portion and the photodetector being mound to head portion, wherein, with the optical assembly housed within the cavity, the head portion is positioned to lie within the head chamber, the tail portion is positioned to lie within the tail chamber, the link is positioned to lie within the intermediate chamber, and the head portion and the tail portion are substantially wider than the intermediate chamber; and wherein the tail portion of the substrate includes an aperture and the housing is formed to further include a post protruding into the tail chamber and through the aperture.

16. The sensor of claim 15, further including an entryway from the exterior of the sensor housing to the cavity, the entryway being in communication with the tail chamber.

17. The sensor the claim 15, further including an entryway from the exterior of the sensor housing to the cavity, the entryway being in communication with the head chamber.

18. A noninvasive pulse oximetry sensor comprising:

a base having an interior base surface and an exterior base surface, the interior base surface being formed to include a channel and a sealing lip substantially surrounding the channel, the channel having a head portion, a tail portion, and an intermediate portion;

an optical assembly having substantially the same shape as the channel and being nested within the channel, the optical assembly comprising a substrate having a head portion, a tail portion, and an intermediate portion, an LED coupled to the tail portion of the substrate, and a photodetector coupled to the head portion of the substrate, wherein the head portion of the substrate is nested within the head portion of the channel, the tail portion of the substrate is nested within the tail portion of the channel, and the intermediate portion of the substrate is nested within the intermediate portion of the channel, and a cover having an interior cover surface and an exterior cover surface, the interior cover surface being formed to include a plateau and a sealing ledge substantially surrounding the plateau, the plateau having a head portion, a tail portion, and an intermediate portion, wherein the sealing ledge is coupled to the sealing lip of the base, thereby nesting the head portion of the plateau within the head portion of the channel, the tail portion of the plateau within the tail portion of the channel, and the intermediate portion of the plateau within the intermediate portion of the channel and sandwiching the optical assembly between the plateau and the channel.

19. The sensor of claim 18, wherein the base includes an entryway in communication with the tail portion of the channel.

20. The sensor of claim 19, wherein the base includes a lug extending into the tail portion of the channel and the cover is formed to include a room in the tail portion of the plateau, the room being formed to receive the lug.

21. The sensor of claim 20, wherein the base includes a post in the head portion of the channel, the optical assembly is formed to include a substrate hole in the head portion of the substrate through which the post extends, and the cover is formed to include a cover hole in the head portion of the plateau to receive an end of the post.

22. The sensor of claim 18, wherein the base includes a lug extending into the tail portion of the channel and the cover is formed to include a room in the tail portion of the plateau to receive the lug.

23. The sensor of claim 18, wherein the base includes a post in the head portion of the channel, the optical assembly is formed to include a substrate hole in the head portion of the substrate through which the post extends, and the cover is formed to include a cover hole in the head portion of the plateau to receive an end of the post.

24. The sensor of claim 23, wherein the base includes a base sidewall bridging between the interior base surface and the exterior base surface and the cover includes a cover sidewall bridging between the interior cover surface and the exterior cover surface such that, when the cover is coupled to the base, the interior base surface abuts the interior cover surface forming a seam there between, the seam being spaced apart from both the exterior base surface and the exterior cover surface.

25. The sensor of claim 18, wherein the base includes a base sidewall bridging between the interior base surface and the exterior base surface and the cover includes a cover sidewall bridging between the interior cover surface and the exterior cover surface such that, when the cover is coupled to the base, the interior base surface abuts the interior cover surface forming a seam there between, the seam being spaced apart from both the exterior base surface and the exterior cover surface.

26. The sensor of claim 18, wherein the cover further includes a first window providing first passageway between the interior cover surface and the exterior cover surface and a second window providing a second passageway between the interior cover surface and the exterior cover surface, and wherein the base further includes mounting members coupled to the exterior base surface which are substantially aligned with the windows of the cover when the cover is coupled to the base.

27. A method for manufacturing a noninvasive pulse oximetry sensor comprising the steps of:

providing a base having an interior base surface and an exterior base surface, the interior base surface being formed to include a channel and a sealing lip substantially surrounding the channel, inserting an optical assembly into the channel, the optical assembly including an LED and a photodetector, providing a cover having an interior cover surface and an exterior cover surface, the interior cover surface being formed to include a plateau and a sealing ledge substantially surrounding the plateau, the cover further including a first window providing a first passageway between the interior cover surface and the exterior cover surface and a second window providing a second passageway between the interior cover surface and the exterior cover surface, coupling a first optically clear lens to the interior cover surface over the first window and a second optically clear lens to the interior cover surface over the second window, and coupling the sealing ledge of the cover to the sealing lip of the base, thereby coupling the cover to the base with the optical assembly sandwich there between and the LED aligned with the first window and the photodetector aligned with the second window.

28. The method as set forth in claim 27, wherein the base includes a lug extending into the channel, the cover includes a room extending into the plateau, and the lug is inserted into the room when the cover is coupled to the base.

29. The method as set forth in claim 28, wherein the base includes a base sidewall bridging between the interior base surface and the exterior base surface and the cover includes a cover sidewall bridging between the interior cover surface and the exterior cover surface such that, when the cover is coupled to the base, the interior base surface abuts the interior cover surface forming a seam there between, the seam being spaced apart from both the exterior base surface and the exterior cover surface.

30. The method as set forth in claim 29, wherein the base further includes mounting members coupled to the exterior base surface which are substantially aligned with the windows of the cover when the cover is coupled to the base.

31. The method as set forth in claim 27, wherein the base includes a base sidewall bridging between the interior base surface and the exterior base surface and the cover includes a cover sidewall bridging between the interior cover surface and the exterior cover surface such that, when the cover is coupled to the base, the interior base surface abuts the interior cover surface forming a seam there between, the seam being spaced apart from both the exterior base surface and the exterior cover surface.

32. The method as set forth in claim 31, wherein the base further includes mounting members coupled to the exterior base surface which are substantially aligned with the windows of the cover when the cover is coupled to the base.

* * * * *

UNITED STATES PATENT AND TRADEMARK OFFICE
CERTIFICATE OF CORRECTION

PATENT NO.    : 6,519,484 B1
DATED         : February 11, 2003
INVENTOR(S)   : David Anthony Lovejoy and George Alexander Byers It is certified that error appears in the above-identified patent and that said Letters Patent is hereby corrected as shown below:

<u>Column 8,</u>
Line 25, insert -- shape as -- after the word "same"
Line 30, insert -- the -- after the word "between"

<u>Column 9,</u>
Line 9, delete "mound to" and insert -- mounted to the --

Signed and Sealed this

Twelfth Day of August, 2003

JAMES E. ROGAN
*Director of the United States Patent and Trademark Office*